(12) United States Patent
Nagano et al.

(10) Patent No.: US 6,767,729 B1
(45) Date of Patent: Jul. 27, 2004

(54) ENZYME LIQUOR AND PROCESS FOR PRODUCING THE SAME ENZYME PREPARATION PROTEASE PREPARATIONS AND PROTEASE-PRODUCING BACTERIUM

(75) Inventors: Hiroko Nagano, Aichi (JP); Zenya Shoji, Akita (JP); Kenichi Hirano, Gifu (JP); Keiichi Ando, Gifu (JP)

(73) Assignee: Amano Enzyme Inc., Nagoya (JP)

( * ) Notice: Subject to any disclaimer, the term of this patent is extended or adjusted under 35 U.S.C. 154(b) by 0 days.

(21) Appl. No.: 09/926,623

(22) PCT Filed: May 25, 2000

(86) PCT No.: PCT/JP00/03380
§ 371 (c)(1),
(2), (4) Date: Nov. 27, 2001

(87) PCT Pub. No.: WO00/73429
PCT Pub. Date: Dec. 7, 2000

(30) Foreign Application Priority Data
May 27, 1999 (JP) .......................... 11-148770

(51) Int. Cl.⁷ ............................ C12N 9/48; C12N 9/50; C12N 1/20; C12N 9/54
(52) U.S. Cl. ................... 435/212; 435/219; 435/183; 435/221; 435/252.5
(58) Field of Search .................. 435/183, 219, 435/212, 221, 252.1

(56) References Cited

U.S. PATENT DOCUMENTS 3,507,750 A * 4/1970 Murray et al.
3,542,563 A * 11/1970 Murray et al.
6,300,116 B1 * 10/2001 von der Osten et al.

FOREIGN PATENT DOCUMENTS

| | | | |
|---|---|---|---|
| CA | 837576 | * | 12/1966 |
| CA | 837543 | * | 6/1967 |
| DE | 003328882 | * | 2/1985 |
| EP | 0 859 050 A | | 8/1998 |
| JP | 55135553 | * | 10/1980 |
| JP | 02-255087 | | 10/1990 |
| JP | 3-123484 | | 5/1991 |
| JP | 05276899 | * | 10/1993 |
| JP | 11-75765 | | 3/1999 |
| SU | 614113 | * | 6/1978 |

OTHER PUBLICATIONS

To, K.A., et al., "Isolation of a Collagenase–Producing Bacterium from Traditional Fermented Food and Its Enzyme Production", Journal of Home Economics of Japan (1997), vol. 48, No. 121, p. 1083–1087.

Eijsink V. G. H. et al., "Thermostability of Bacillus subtilis neutral protease." BIOCHEM. INT., vol. 24, No. 3, Jun. 1991 (1991–06), pp. 517–525, XP00619254.

Wang et al., "Thermostable alkaline lipase from a newly isolated thermophilic Bacillus. strain A30–1 (ATCC 53841).", J. FERMENT. BIOENG., vol. 79, No. 5, 1995, pp. 433–438, XP002036572.

Nagano H. et to K.A., "Purification of collagenase and specificity of its related enzyme from Bacillus subtilis FS–2.", BIOSCI. BIOTECHNOL> BIOCHEM., bol. 63, No. 7, Jan. 2000 (2000–01), pp. 181–183, XP009011014.

* cited by examiner

*Primary Examiner*—Michael Meller
(74) *Attorney, Agent, or Firm*—Oblon, Spivak, McClelland, Maier & Neustadt, P.C.

(57) ABSTRACT

An enzyme solution obtained by cultivating *Bacillus subtilis* M2-4 strain highly heat-resistant peptidase activity such that the residual activity thereof after 1-hr heat treatment at 60 to 65° C. at pH 7 is substantially 100%. An enzyme preparation can be obtained by separating the enzyme protein from the enzyme solution. Using such enzyme solution or enzyme preparation as an active component, a proteolytic enzyme preparation can be prepared. The enzyme solution, the enzyme preparation and the proteolytic enzyme preparation have both high heat-resistance and great potency of hydrolyzing proteins into low molecules.

7 Claims, 4 Drawing Sheets

FIG. 1

| | His | Arg | Asn | Gln | Ser | Asp | Gly | Glu | Thr | Ala | Pro | Met | Val | Cys | Lys | Phe | Ile | Leu |
|---|---|---|---|---|---|---|---|---|---|---|---|---|---|---|---|---|---|---|
| M2-4 | | ← | ← | ← | ← | | ← | | ← | ← | | | ← | | ← | ← | ← | ← |
| PROLEATHER | | | | ← | ← | | | | ← | ← | | | | | ← | ← | | ← |
| PROTEASE N | | | | | | | | | ← | | | | | | | ← | | ← |

ENZYME LIQUOR AND PROCESS FOR PRODUCING THE SAME ENZYME PREPARATION PROTEASE PREPARATIONS AND PROTEASE-PRODUCING BACTERIUM

TECHNICAL FIELD

The present invention relates to an enzyme solution and a method for producing the same, an enzyme preparation obtained from the enzyme solution, a proteolytic enzyme preparation containing the enzyme solution or the enzyme preparation as an active component, and a strain producing the proteolytic enzyme.

BACKGROUND OF THE INVENTION

In extremely diversified industrial fields, techniques of hydrolyzing various proteins into peptides or amino acids have been utilized widely. The techniques are applied to the preparation of, for example, medical enteric formulas and nutritious supplements as food materials. The techniques are also applied to increase the food utilization efficiency by enhancing the efficiency of hydrolyzing proteins hard to be hydrolyzed, which are contained in soybean protein and the like. Further, the techniques are utilized for the preparation of amino acid seasoning from proteins as raw materials. Still further, the techniques are utilized for the preparation of bread with enhanced rise.

Although chemical degradation methods using hydrochloric acid and the like so as to hydrolyze protein are efficient, the methods may result in the formation of undesirable by-products because of severe hydrolyzing conditions. Particularly in industrial fields of foods, seasonings, materials for nutrition and the like relating to human bodies, methods capable of hydrolyzing protein under mild conditions are prefered (for example, Japanese Patent Publication No. Hei-7-53106, Japanese Patent Laid-open No. Hei-11-75765, and the like).

Herein, proteolytic enzymes for industrial use for the purposes described above have been produced so far, mainly by means of various bacteria and fungi. However, it is generally said that proteolytic enzymes obtained from bacteria and those obtained from fungi have both advantages and disadvantages. Actually, proteolytic enzymes for industrial use having sufficient activity and stability have not been available.

In other words, bacteria-derived proteolytic enzymes generally have good heat resistance but have low peptidase activity for hydrolyzing protein into amino acids, or low potency of hydrolyzing proteins into low molecules. Therefore, the degradation products obtained by using bacteria-derived proteolytic enzymes contain great amounts of high-molecular peptides. Hence, such products have a disadvantage in that the bitterness thereof as food materials, seasonings and the like is strong, and in that the intestinal absorption thereof as materials for nutrition is slow. Although bacteria-derived proteolytic enzymes have good heat resistance, there has hardly been reported such proteolytic enzyme with high heat resistance that can retain peptidase activity, for example, in a high temperature range of about 60° C.

In contrast, fungi-derived proteolytic enzymes are generally excellent in peptidase activity, wide cleavage specificity of peptide bond, potency of hydrolyzing proteins into low molecules and the like. However, the heat resistance, for example, the potency of protein hydrolysis in a moderate to high temperature range of about 50° C. or higher, is poor. Therefore, such proteolytic enzymes essentially require protein hydrolyzing steps in a relatively low temperature range, readily allowing the propagation of contaminated microorganisms.

As described above, there have not been provided proteolytic enzymes with high thermal stability such that the enzyme is never inactivated in moderate to high temperature ranges and also with great potency of hydrolyzing proteins into low molecules.

Further, it is desired to effectively hydrolyze proteins hard to be hydrolyzed, such as those contained in soybeans and the like, as useful protein materials. It is thus important that proteolytic enzymes have wide cleavage specificity for peptide bonds in protein. However, no proteolytic enzyme has been provided, which has both the thermal stability and the great potency of hydrolyzing proteins into low molecules and which additionally has high potency of hydrolyzing proteins hard to be hydrolyzed.

DISCLOSURE OF THE INVENTION

The present inventors cultivated a bacterium of genus Bacillus, which was isolated from the dough of "Mantou (a kind of Asian steamed buns)" as one of traditional foods in the Mongol District. It was then found that the enzyme solution consequently obtained had the enzyme characteristics as described above.

Based on the findings, the invention provides a proteolytic enzyme solution with thermal stability in moderate to high temperature ranges and with excellent potency of hydrolyzing proteins into low molecules as well. Further, the invention provides a proteolytic enzyme solution additionally having the potency of effectively hydrolyzing protein hard to be hydrolyzed. Still further, the invention provides a method for producing such enzyme solution. Further, the invention provides an enzyme preparation obtained by separating the enzyme protein from the enzyme solution. And yet further, the invention provides a proteolytic enzyme preparation containing the enzyme preparation as the active component, which can be used for given uses. Still further, the invention provides a strain producing proteolytic enzyme to prepare the enzyme solution and the enzyme preparation.

The enzyme solution of the invention is an enzyme solution with proteolytic activity, which can be obtained by cultivating a bacterium of the genus Bacillus, and has such highly heat-resistant peptidase activity that the residual activity of the enzyme after 1-hour heat treatment at 60 to 65° C. at pH 7 is substantially 100%. The use of the enzyme solution enables the protein hydrolyzing process under temperature conditions never permitting the propagation of contaminated microorganisms, for example at 50° C. or higher, or in moderate to high temperature ranges up to 60 to 65° C. Further, the peptidase activity can allow sufficient potency of hydrolyzing proteins into low molecules. The peptidase activity is more preferably an aminopeptidase activity.

More preferably, the enzyme solution of the invention additionally has protease activity and collagenase activity in combination. The protease activity includes neutral protease activity with favorable pH within the neutral region and alkaline protease activity with favorable pH within the alkaline region. Such enzyme solution can be expected of more excellent potency of hydrolyzing proteins into low molecules and the large initial reaction velocity as a general characteristic of protease activity. Therefore, proteolytic reaction can be speedily promoted. For meat tenderization, for example, meat tenderization by the peptidase activity and the protease activity can progress, simultaneously with the cleavage of collagen in the connective tissues by the collagenase activity, so that very tasty meat can be prepared.

Still more preferably, the enzyme solution of the invention has at least one of the following characteristics 1) to 4) so as to provide additional effects described below.

1) Enzyme solution with peptide cleavage site specificity capable of cleaving sites of at least ten amino acid types bonded in the peptide chain of protein. Regarding such wide range of peptide cleavage site specificity, peptide cleavage site specificity capable of cleaving 10 or more, preferably 12 amino acid types bonded at the carboxyl termini can be observed. Such amino acid types specifically include leucine, isoleucine, phenylalanine, lysine, valine, alanine, threonine, glycine, serine, glutamine, asparagine and arginine.

Typically, general proteolytic enzymes have peptide cleavage site specificity capable of substantially cleaving 5 to 6 or less, at most less than 10 amino acid types bonded. Therefore, the peptide cleavage site specificity of the enzyme solution covers a very wide range. Thus, the enzyme solution can retain great potency of hydrolyzing proteins into low molecules. Probably owing to the wide range of peptide cleavage site specificity, the enzyme solution has effective proteolytic activity over proteins, such as those derived from for example soybeans, which have been so far hard to be hydrolyzed.

2) Enzyme solution with such potency of hydrolyzing proteins into low molecules that the 17-hr hydrolysis by use of the enzyme solution of 200 units on a protease activity basis per 1 g of acid casein generates peptides or amino acids with molecular weights of 1,000 or below in an amount of 50% by weight or more relative to the acid casein. Regarding the potency of hydrolyzing proteins into low molecules, it has been found that the amounts of generated peptides or amino acids with molecular weights not exceeding 1,000 are prominently large, compared with conventional proteolytic enzymes.

Owing to such characteristics of the enzyme solution, the enzyme solution can efficiently generate peptides or amino acids with molecular weights not exceeding 1,000 from raw protein materials. Hence, high-quality amino acid materials and amino acid seasonings without bitterness can be prepared. Further, materials for nutrition with great absorbency from the digestive tract can be prepared.

3) Enzyme solution with the potency of hydrolyzing proteins into low molecules as described above in 2), that is exerted equally under temperature conditions of 45° C. close to the relatively moderate temperature range and 60° C. in a fairly high temperature range. Owing to such characteristics of the enzyme solution, the process of hydrolyzing proteins into low molecules can be progressed under temperature conditions never permitting the propagation of contaminated microorganism.

4) Enzyme solution with a 50% or more of solubilization ratio of soybean protein hard to be hydrolyzed under given conditions. It is expected that this proteolytic activity to hydrolyze protein hard to be hydrolyzed is also effective for hydrolyzing proteins in other species, such as meat connective tissue. This characteristic may possibly be related to the wide range of peptide cleavage site specificity, particularly cleavage site specificity to bonded sites of amino acid, such as glycine, valine and asparagine, which has not been found in conventional proteolytic enzymes.

Owing to such characteristic property, the enzyme solution can effectively hydrolyze soybean useful as a raw protein material, including its protein hard to be hydrolyzed, into amino acids.

The enzyme solution of the invention can readily and securely be obtained by cultivating a given bacterium of the genus Bacillus. The enzyme solution can be obtained by cultivating for example *Bacillus subtilis* M2-4 strain internationally deposited as FERM BP-7155 under the Budapest Treaty. The cultivation conditions therefor are not specifically limited. The strain may satisfactorily be cultivated by using general nutritious culture media under general conditions, and may also be cultivated in a specific culture medium under specific cultivation conditions, if necessary.

As the enzyme solution, a liquid culture medium where the strain is cultivated can be used without removing bacteria. Otherwise, an enzyme solution prepared by removing the bacteria or solids therefrom by means of filtration or centrifugation can also be used. The enzyme solution may further be concentrated by mild means using an ultrafiltration membrane.

From the enzyme solutions described above in accordance with the invention are obtained plural types of protein fractions with different molecular weights by column chromatography. By individually separating the proteins in these individual fractions and subjecting the proteins to enzyme activity test, it was confirmed that the enzyme solution contained aminopeptidase, neutral protease, acid protease and collagenase. Hence, the highly heat-resistant peptidase activity, protease activity, collagenase activity and the characteristics 1) to 4) described above are essentially based on the actions of these enzymes. However, how and to what extent each of the enzymes is involved in the individual characteristics 1) to 4) described above have not yet been identified accurately.

The invention further provides a method for producing an enzyme solution, comprising cultivating a bacterium of the genus Bacillus, and obtaining the enzyme solution of the invention from the culture. The method for producing an enzyme solution enables ready and secure obtainment of the enzyme solution.

Further, the invention provides an enzyme preparation obtained by separating the enzyme protein from the enzyme solution. For the separation of the enzyme protein, the enzyme protein can be separated by known appropriate processes, such as salting out of the enzyme solution under the saturation of ammonium sulfate and ethanol precipitation. The enzyme preparation may be obtained as crude enzyme powder or formulations of buffer solutions thereof. The enzyme preparation is advantageous in that the high-quality preparation is made more easily, compared with the enzyme solution. These enzyme preparations have the same enzyme activity and characteristics as those of the enzyme solution.

Still further, the invention provides a proteolytic enzyme preparation containing the enzyme solution or the enzyme preparation as the active component, which can be used for any of uses, such as hydrolysis of protein hard to be hydrolyzed, production of amino acid seasoning, bread production, meat tenderization, peptide production, production of protein with reduced allergenicity and cheese production.

The proteolytic enzyme preparation has highly heat-resistant peptidase activity, excellent potency of hydrolyzing proteins into low molecules, collagenase activity and the like in the above-mentioned various uses, which have not been found in the conventional proteolytic enzyme preparations. For use in bread production, the proteolytic enzyme preparation brings about an effect of volume increase (enhancement of rising).

Furthermore, the invention provides a strain producing proteolytic enzyme. The proteolytic-enzyme-producing strain provides effective means for producing the variety of the enzyme solution, the enzyme preparation and the proteolytic enzyme preparation. The proteolytic-enzyme-producing strain belongs to the genus Bacillus and is preferably a bacterium of the species *subtilis*. The most typical proteolytic-enzyme-producing strain is *Bacillus subtilis* M2-4 strain.

The *Bacillus subtilis* M2-4 strain was deposited as FERM P-17388 at the National Institute of Bioscience and Human-Technology Agency of Industrial Science and Technology, the Ministry of International Trade and Industry (Address: 1-1-3, Higashi, Tsukuba, Ibaraki, Japan) on May 12, 1999. Then, the strain was transferred to the International Deposit as FERM BP-7155 on May 11, 2000 under the Budapest Treaty.

The *Bacillus subtilis* M2-4 strain is practically very useful, in particular, among plural species of strains producing proteolytic enzyme, which are isolated from the dough of Mantou, a traditional naturally fermented wheat food in the Mongol District. As a result of the identification test, it was found that the M2-4 strain exhibited the growth state in Table 1 (colony cultivated in the general agar culture medium manufactured by Eiken Chemical Co., Ltd. at 30° C. for 48 hours) The bacteriological morphology in Table 2 was also observed. Further, it was found that the strain exerted the physiological properties in Table 3.

TABLE 1

| Item | M2-4 strain |
| --- | --- |
| Morphology | circular |
| Surface | smooth |
| Edge | entire |
| Elevation | flat |
| Transparency | opaque |
| Gloss | dull |
| Color | yellowish white to cream color |

TABLE 2

| Item | Cultivation temperature | Cultivation period | M2-4 strain |
| --- | --- | --- | --- |
| Cell: morphology dimension | 30° C. | 24 hours | rod 2.4 to 3.0 × about 0.8μ |
| Mobility | 25° C. | 24 hours | having peritrichous flagella with mobility |
| Spore: morphology sporangium swollen spore location | 30° C. | 48 hours | oval not swollen central or subterminal to terminal |

TABLE 3

| Item | M2-4 strain |
| --- | --- |
| Gram staining | + |
| Catalase | + |
| Anaerobic growth | − |
| Voges-proakauer reaction V-P broth | + |
| at pH below 6 | + |
| at pH above 7 | − |

TABLE 3-continued

| Item | M2-4 strain |
| --- | --- |
| Acid generation | |
| D-glucose | + |
| L-arabinose | + |
| D-xylose | + |
| D-mannitol | + |
| Gas generation from glucose | − |
| Hydrolysis | |
| Casein | + |
| Gelatin | + |
| Starch | + |
| Utilization of citric acid | + |
| Utilization of propionic acid | − |
| Hydrolysis of Tyrosine | − |
| Egg-yolk reaction | − |
| Phenylalanine deaminase | − |
| Reduction of nitrate salt | + |
| Indole generation | − |
| Glucose-added Culture medium | + |
| black pigment | − |
| Growth at pH 6.8 | + |
| Growth at pH 5.7 | + |
| Growth in culture medium with sodium chloride at | |
| 2% | + |
| 5% | + |
| 7% | + |
| 10% | + |
| Growth temperature | |
| 5° C. | − |
| 10° C. | − |
| 30° C. | + |
| 40° C. | + |
| 50° C. | + |
| 55° C. | − |

Based on the above-mentioned grounds, the bacterial strain was identified to belong to "*Bacillus subtilis*" and was designated "*Bacillus subtilis* M2-4 strain".

BRIEF DESCRIPTION OF THE DRAWINGS

FIG. 1 is a chart depicting the peptide cleavage site specificities of enzymes.

BEST MODE FOR CARRYING OUT THE INVENTION

Best mode for carrying out the invention is now described below, together with comparative examples. The invention is not limited to these modes for carrying out the invention.

EXAMPLE 1

Preparation of Enzyme Solution and Contents Analysis

A culture medium was prepared, which comprised 1% glucose, 1% peptone, 0.3% gelatin, 0.1% yeast extract, 0.7% dipotassium phosphate, 0.1% monopotassium phosphate, 0.05% citric acid and 0.01% magnesium sulfate. 100 mL of the culture medium was placed in a 500 mL Sakaguchi flask for sterilization at 120° C. for 20 minutes. Subsequently, the *Bacillus subtilis* M2-4 strain was inoculated in the culture medium for cultivation with shaking incubator at 30° C. for 40 hours. After cultivation with shaking incubator, the culture broth in the flask was centrifuged to remove the bacteria, so as to prepare a crude enzyme solution.

Figure 2:
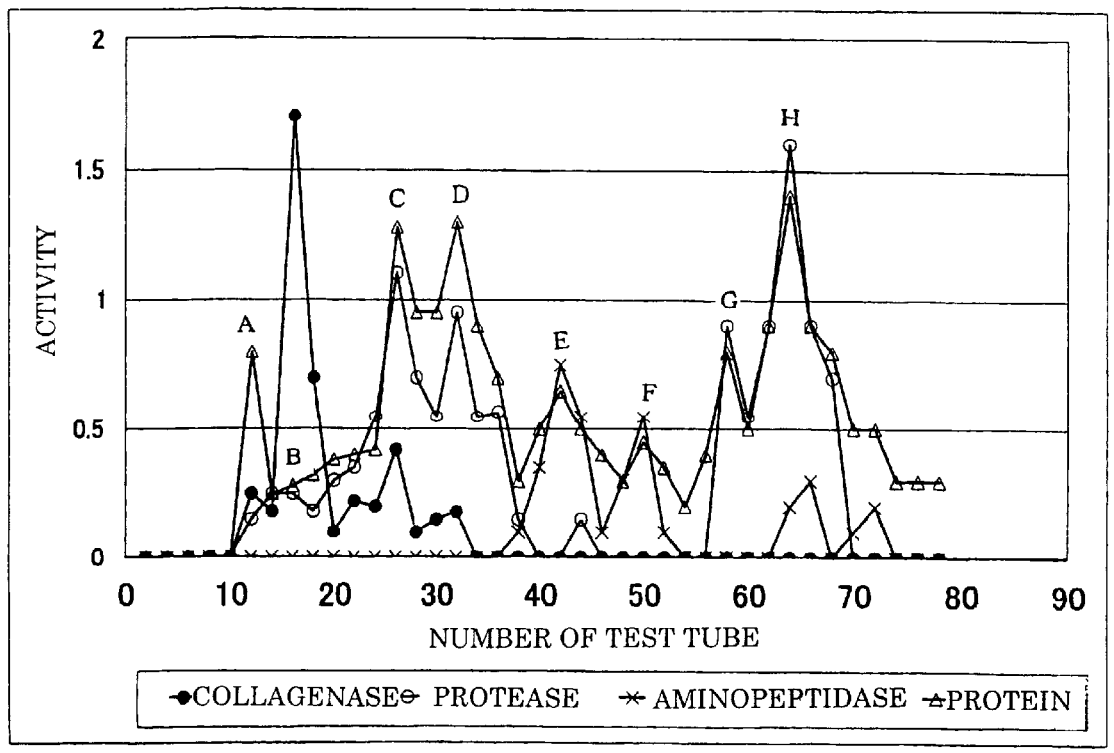
FIG. 2 depicts a chromatographic chart of the example.

The crude enzyme solution was subjected to chromatography on a column "DEAE Sepharose CL6B". As shown in FIG. 2, plural peaks A to H were observed in extracted fractions of molecular weights showing protein.

The fractions corresponding to the individual peaks were separately obtained and subjected to various enzyme activity tests. Consequently, it was confirmed that the solution obtained from the peak B contained collagenase. It was confirmed that the solutions obtained from the peaks C and D contained alkaline protease. It was confirmed that the solutions obtained from the peaks E and F contained aminopeptidase. It was confirmed that the solutions obtained from the peaks G and H contained neutral protease. The activities of the enzymes were individually assayed by the following methods.

Protease Activity:

1 mL of a solution obtained from a peak fraction was added to 1 mL of 0.75% milk casein solution (pH 7.0) for reaction at 37° C. for 60 minutes. Subsequently, 2 mL of 0.4 M trichloroacetic acid solution was added to terminate the enzyme reaction. The solution was left to stand at 37° C. for 25 minutes, and then filtered through a filter paper. 1 mL of the filtrate was added to 5 mL of 0.4 M sodium carbonate solution separately prepared, followed by further addition of 1 mL of Folin reagent (manufactured by Wako Pure Chemical Industries, Ltd.), and the resulting mixture solution was left to stand at 37° C. for 20 minutes. The absorbance of the solution was measured at 660 nm. At the blank test, the reaction comprised adding 2 mL of 0.4 M trichloroacetic acid solution and subsequently adding 1 mL of the solution obtained from the fraction according to the procedures. Under the reaction conditions, the activity to generate amino acid corresponding to 0.1 mg tyrosine in the filtrate was defined as one unit.

Collagenase Activity:

0.1 mL of a solution obtained from a fraction was added to 0.4 mL of 2.5% collagen solution (pH 7.5) for reaction at 30° C. for 30 minutes. Subsequently, 0.5 mL of 0.1 M acetic acid solution was added. Centrifuging the solution, the supernant was obtained. To 0.1 mL of the supernant were added 0.9 mL citrate buffer, pH 5, 0.1 mL of tin chloride solution and 2 mL of ninhydrin solution, for heating in boiling water for 20 minutes. Subsequently, water was added to the resulting mixture to 10 mL, and the absorbance of the resulting mixture was assayed at 570 nm. At the blank test, the same assay procedures were performed by using the solution obtained from the peak fraction treated with heating in boiling water for 5 minutes. Under the reaction conditions, the activity to generate amino acid corresponding to 1 $\mu$mol tyrosine per one minute was defined as one unit.

Aminopeptidase Activity:

0.1 M Tris buffer (pH 7.0) was added to 0.8 mL of leucine-p-nitroanilide solution (0.072%), followed by addition of 0.2 mL of a solution obtained from each peak fraction, for reaction at 37° C. for 60 minutes. Subsequently, 2 mL of 0.7% hydrochloric acid/ethanol solution was added, followed by addition of 2 mL of 0.06% p-dimethylamino.cinnamic aldehyde solution. 10 minutes later, the absorbance at 540 nm was assayed. At the blank test, the same assay procedures were performed by using the solution obtained from the peak fraction treated with heating in boiling water for 5 minutes. Under the reaction conditions, the activity to generate 1 $\mu$mol leucine per one minute was defined as one unit.

Figure 3:
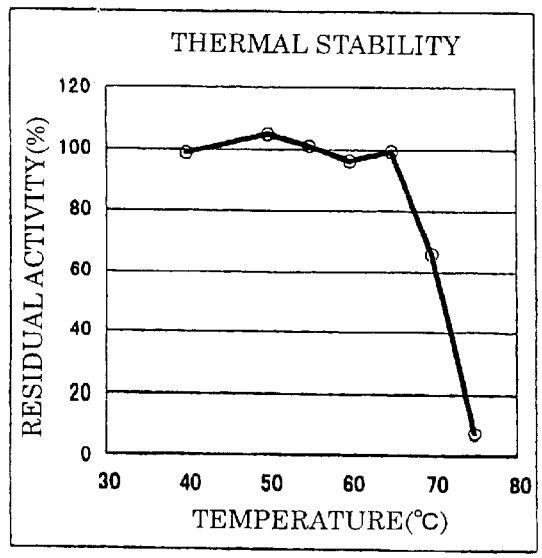
FIG. 3 depicts a graph of the thermal stability of enzyme.

Among solutions obtained from the fractions corresponding to the individual peaks, the solutions obtained from the peaks E and F were concentrated with a UF membrane of a fractionating molecular weight of 3,000 (Minitan plate manufactured by Amicon Co., Ltd.) to evaluate the thermal stability of aminopeptidase. As shown in FIG. 3, the residual activity of the aminopeptidase after 1-hr heat treatment at temperatures from 40° C. to 65° C. at pH 7 was almost 100% in any of the cases.

EXAMPLE 2

Preparation of Concentrated Enzyme Solution

The *Bacillus subtilis* M2-4 strain was separately inoculated in 20 Sakaguchi flasks, each containing 100 mL of a culture medium of the same composition as in Example 1. Under the same conditions as in Example 1, the strain was cultivated with shaking incubator and centrifuged to remove the bacteria, thereby to prepare a crude enzyme solution. Subsequently, these enzyme solutions were put together (about 1,900 mL in total). In the crude enzyme solution, the neutral protease activity was 11.0 u/mL; alkaline protease activity, 12.1 u/mL; collagenase activity, 4.4 u/mL; and aminopeptidase activity, 0.48 u/mL.

Then, about 1,900 mL of the crude enzyme solution was concentrated with a membrane Minitan plate (fractionating molecular weight of 3,000) manufactured by Amicon Co., Ltd., to obtain about 90 mL of the concentrated enzyme solution. In the crude enzyme solution, the neutral protease activity was 166 u/mL; alkaline protease activity, 180 u/mL; collagenase activity, 66.4 u/mL; and aminopeptidase activity, 5.9 u/mL.

EXAMPLE 3

Preparation of Enzyme Preparation

20 L of a culture medium with the same composition as in Example 1 was placed in a 30-L jar fermenter. Then, the *Bacillus subtilis* M2-4strain was cultivated for 40 hours under conditions of 30° C., a rotation number of 250 rpm, and an aeration volume of 20 L/min.

After cultivation, the culture was centrifuged to remove the bacteria and to obtain 18 L of the resulting solution, which was then concentrated with a UF membrane (fractionating molecular weight of 13,000) manufactured by Asahi Chemical Industry Co., Ltd. to 900 mL. The concentrate was salted out by saturating to 0.8 using ammonium sulfate. The generated precipitate was freeze-dried, to obtain an enzyme preparation comprising 75 g of the crude enzyme powder.

The enzyme activity of the enzyme preparation was as follows. The neutral protease activity was 1,992 u/mL; alkaline protease activity, 2,200 u/mL; collagenase activity, 790 u/mL; and aminopeptidase activity, 71 u/mL.

EXAMPLE 4

Potency of Hydrolyzing Proteins into low Molecules 200 units (on the activity basis of protease, pH 7 per 1 g of acid casein) of the enzyme preparation prepared in Example 3 was added to 1% acid casein solution, pH 7. For comparison, 200 units (on the activity basis of protease, pH 7 per 1 g of acid casein) of the neutral protease from *Bacillus subtilis*, namely "Protease N" (manufactured by Amano Pharmaceutical Company, Ltd.) was added to 1% acid casein solution, pH 7. Further, 200 units (on the activity basis of protease, pH 7 per 1 g of acid casein) of the alkaline protease from *Bacillus subtilis*, namely "Proleather" (manufactured by Amano Pharmaceutical Company, Ltd.) was added to 1% acid casein solution, pH 7. The individual solutions of the added enzymes were subjected to hydrolyzing reaction at 45° C. for 17 hours, to assay the molecular weight distribution of the resulting reaction products.

The assay was done by gel filtration, using an FPLC system manufactured by Amersham and an analysis column "Superose 12" manufactured by Amersham. As the standard substances for molecular weights, serum albumin (molecular weight of 67,000), chymotrypsinogen (molecular weight of 25,000), cytochrome C (molecular weight of 12,300), trypsin inhibitor (molecular weight of 6,500) and bacitracin (molecular weight of 1,450) were used.

Figure 4:
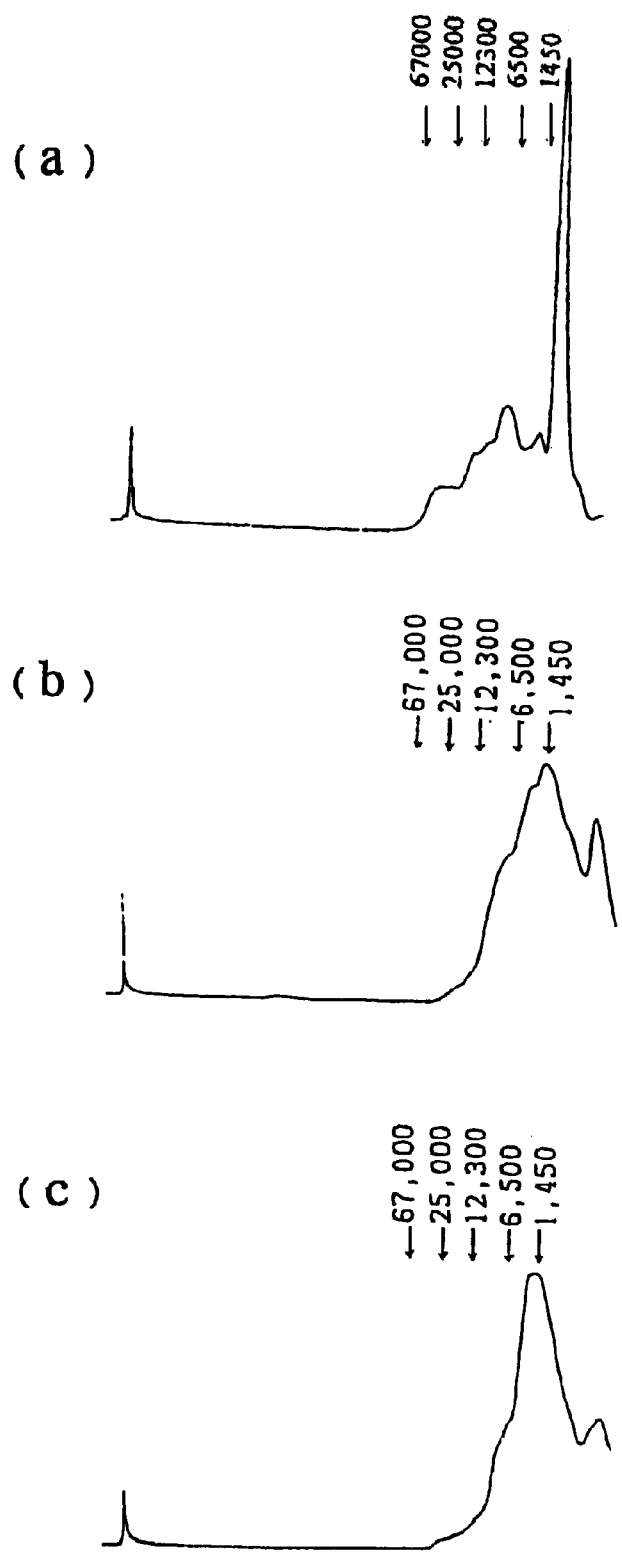
FIG. 4 depicts graphs of molecular weight distributions of hydrolyzed products.

The assay results with the enzyme preparation of the Example are shown in (a) of FIG. 4; the assay results with Proleather are shown in (b) of FIG. 4; and the assay results with Protease N are shown in (c) of FIG. 4.

As apparently shown in (b) and (c) of FIG. 4, the peptides obtained by using Proleather and Protease N mainly include a larger amount of high molecular peptides with molecular weights above 1,000 to 10,000, and include a smaller amount of low molecular peptides with molecular weights of 1,000 or less. In any case, the quantity ratio X/Y of the higher molecular peptides (X) to the lower molecular peptides (Y) was about 4 or larger.

As indicated in (a) of FIG. 4, in contrast, the peptides obtained by using the enzyme preparation of the Example are mostly composed of low molecular peptides with molecular weights of 1,000 or less. The quantity ratio X/Y of the higher molecular peptides (X) to the lower molecular peptides (Y) was 0.7 or less, and the result was prominently different from the results in (b) and (c) of FIG. 4.

It is said that the low molecular peptides with molecular weights of 1,000 or less are effective as medical enteric formulas and nutritious supplements as food materials, owing to its rapid absorption from the digestive tracts. The peptides obtained by using the enzyme preparation of the Example satisfy such purposes.

EXAMPLE 5

Potency of Hydrolyzing Proteins into Low Molecules in High Temperature Zone 200 units (on the activity basis of protease, pH 7 per 1 g of acid casein) of enzyme preparation prepared in Example 3 was added to 1% acid casein solution, pH 7. For comparison, 200 units (on the activity basis of protease, pH 7 per 1 g of acid casein) of the neutral protease from *Aspergillus oryzae*, namely "Protease A" (manufactured by Amano Pharmaceutical Company, Ltd.) was added to 1% acid casein solution, pH 7. These enzyme solutions were individually subjected to hydrolyzing reaction at 45° C. and 60° C. for 17 hours, to assay the molecular weight distribution of the resulting reaction products. The assay method is the same as in Example 4.

Figure 5:
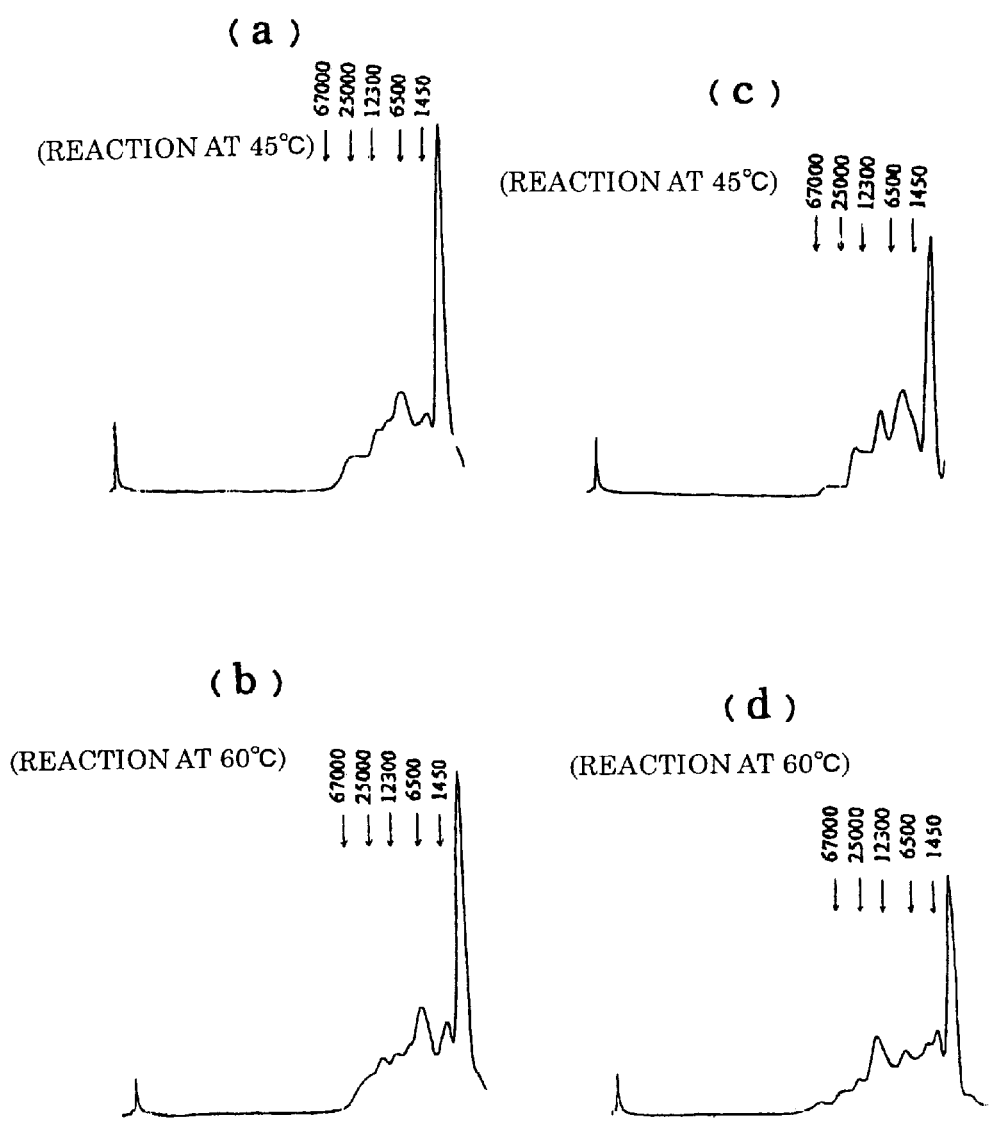
FIG. 5 depicts graphs of molecular weight distributions of hydrolyzed products.

The assay results with the enzyme preparation of the Example in case of reaction at 45° C. and 60° C. are shown in (a) and (b) of FIG. 5, respectively. The assay results with Protease A in case of reaction at 45° C. and 60° C. are shown in (c) and (d) of FIG. 5, respectively.

As apparently shown in (c) of FIG. 5, the peptides obtained using Protease A in case of 45° C. are more likely to include high molecular peptides, as in Example 4. As shown in (d) of FIG. 5, however, the tendency is more distinct in case of 60° C., suggesting fair reduction of the activity of Protease A in such high temperature zone.

As indicated in (a) and (b) of FIG. 5, in contrast, peptides obtained by using the enzyme preparation of the Example brought about almost similar results in case of 60° C. to those in case of 45° C. In other words, low molecular peptides with molecular weights of 1,000 or less mostly occupy the resulting peptides, thus proving that the enzyme preparation has excellent potency of hydrolyzing proteins into low molecules and high heat resistance as well.

For peptide production in an industrial scale using the enzyme preparation of the Example, the process control at 55° C. or higher (for example, 60° C.) is possible, while avoiding the procedures at 50° C. or lower where microbial contamination may occur due to the propagation of contaminated microorganism. Hence, enormous industrial advantages can be attained.

EXAMPLE 6

Hydrolysis of Protein Hard to be Hydrolyzed 100 g of "Newfujipro R" manufactured by Fuji Oil Co., Ltd. as a commercially available soybean protein isolate was dissolved in 1,000 mL of water. To the solution were added 1 g each of "Proleather" and "Protease A", for hydrolyzing reaction at 50° C. for 17 hours. Subsequently, the resultant solution was centrifuged, and the precipitate emerging due to no reaction with the proteases was separated and dried, thereby obtaining 25 g of water-insoluble matters, i.e. the matters hard to be hydrolyzed.

The matters were subjected to protein assay by the Kjeldahl method. The matters contained 20% by weight of protein. 5 g of the dried matters hard to be hydrolyzed was suspended in 100 mL of water, followed by addition of 6 mL of the crude enzyme solution obtained in Example 1 described above, for hydrolyzing reaction at 50° C. for 17 hours.

For comparison, 0.1 g of Proleather was added to 100 mL each of the suspensions of the matters hard to be hydrolyzed prepared in the same manner as described above. In the same manner, 0.1 g of Protease A was added to prepare a mixture solution. These solutions were also subjected to hydrolyzing reactions under the same conditions as described above.

After termination of the reactions of the individual examples and subsequent centrifugation, the protein in the supernatants was assayed by the Kjeldahl method to calculate the solubilization ratio of the protein hard to be hydrolyzed. The solubilization ratio of the example with Proleather was 5%, while the solubilization ratio of the example with Protease A was 4%. On the other hand, the solubilization ratio of the example with the crude enzyme solution of the Example was 70%.

The crude enzyme solution can therefore be used to effectively hydrolyze protein hard to be hydrolyzed, for peptide or amino acid production using protein materials including such protein. Consequently, the use thereof can improve the peptide yield and reduce the quantity of waste.

EXAMPLE 7

Peptide Cleavage Site Specificity

The enzyme preparation prepared in Example 3, and Proleather and Protease N for comparison were respectively added in equal unit quantities to 1% acid casein solution, pH 7 for hydrolyzing reaction. Subsequently, yeast carboxypeptidase Y was added to the reaction solution of each example to analyze free amino acids so as to infer the carboxyl termini of the cleaved peptides.

As marked with arrows in the corresponding columns in FIG. 1, Protease N cleaved the carboxyl sides of three types of amino acids, namely leucine, phenylalanine and threonine. Proleather cleaved the carboxyl sides of six types of amino acids, namely leucine, phenylaianine, lysine, alanine, serine and glutamine. In contrast, the enzyme preparation of the Example as expressed as "M2-4" cleaved the carboxyl sides of 12 types of amino acids, namely leucine, isoleucine, phenylalanine, lysine, valine, alanine, threonine, glycine, serine, glutamine, asparagine and arginine. In other words, it was found that the enzyme preparation of the Example exerted cleavage specificity in a very wide range of peptide sites.

It is assumed that the cleavage specificity in a very wide range of peptide sites may have relationship with the potency of hydrolyzing proteins into low molecules and the potency of hydrolysis of protein hard to be hydrolyzed, as exerted by the enzyme solution and enzyme preparation of the invention.

EXAMPLE 8

Production of Amino Acid Seasoning

The enzyme preparation prepared in Example 3, and Proleather and Protease A for the comparison were separately added to 10% acid casein solution, pH 7, finally to 200 units on the basis of the protease activity, pH 7 per 1 g of acid casein. After separate cleavage reaction at 55° C. for 17 hours, further, the supernatant obtained via centrifugation was subjected to amino acid analysis and sensory taste assessment.

In the example with Proleather, the amount of free amino acids generated in the supernatant was 15%, and the supernatant was bitter with poor Umami (deliciousness). In the example with Protease A, the amount of free amino acids generated in the supernatant was 36%, and the supernatant was slightly bitter with poor Umami (deliciousness). In the example with the enzyme preparation of the Example, the amount of free amino acids generated in the supernatant amounted to 46%, and the supernatant was with great Umami (deliciousness).

EXAMPLE 9

Production of Chinese Mantou(a Kind of Asian Steamed Buns)

10 g of sugar and one gram of salt were added to 100 g of highly gluten-rich flour and 100 g of flour at a low gluten level, followed by addition of 105 mL of warm water at 30° C., for thorough mixing. To the mixture were added 2.0 mL of the crude enzyme solution prepared in Example 1 and 4 g of a commercially available baker's yeast (manufactured by Oriental Yeast Co., Ltd.), for primary fermentation at 30° C. for 4 hours. Then, the mixture was divided into 20 g portions, which were then molded for secondary fermentation at 30° C. for 4 hours. Subsequently, the resulting dough was steamed on a boiling hot water bath for 6 minutes to prepare Chinese Mantou.

For comparison, 4 g of the commercially available baker's yeast (manufactured by Oriental Yeast Co., Ltd.) was singly added to the mixture to prepare Chinese Mantou by the same method.

The volumes of the Chinese Mantou pieces prepared in accordance with the Example and the comparative example were measured. It was found that the volume of the Chinese Mantou with addition of the enzyme solution of the Example was larger by about 15% than the volume of the Chinese Mantou without any addition of the enzyme solution for comparison.

EXAMPLE 10

Production of Bread 100 g of flour, 50 g of sugar, 20 g of salt, 40 g of shortening and 30 g of a commercially available baker's yeast (manufactured by Oriental Yeast Co., Ltd.) were mixed together. To the resulting mixture were added 690 mL of water and 50 mL of the crude enzyme solution prepared in Example 1, for kneading at 27 to 29° C. After 30-min primary fermentation, the resulting dough was divided into 450 g portions for secondary fermentation for 30 minutes. Each dough was placed in a bread pan for baking at 230° C. for 25 minutes.

For comparison, the mixture without any addition of the enzyme solution was subjected to primary fermentation, secondary fermentation and baking by the same methods as described above.

The volumes of the prepared breads of the Example and and the comparative example were measured. It was found that the volume of the bread with addition of the enzyme solution as the Example was large by about 10%, compared with the volume of the bread without any addition of the enzyme solution.

EXAMPLE 11

Application to Yeast Extract

Water was added to 100 g of a commercially available dry baker's yeast (manufactured by Oriental Yeast Co., Ltd.) to one liter. After the resulting solution was adjusted to pH 7 by means of 2 M hydrochloric acid solution, the solution was heated at 90° C. for 30 minutes. To the resulting solution was added 1 g of a cell lytic enzyme "YL-15" (manufactured by Amano Pharmaceutical Company, Ltd.), and the resulting mixture was allowed to react together with agitation at 50° C. for 16 hours. Subsequently, the yeast bacteria were subjected to lysis with heating at 90° C. for 20 minutes to obtain the extract solution. After centrifugation of the extract solution and freeze-drying of the supernatant, a yeast extract powder of 70 g was obtained. The protein content of the powder was 35%.

7 g of the obtained yeast extract powder was dissolved in 100 mL of water. The resulting solution was adjusted to pH 7, by means of 2 M hydrochloric acid, to prepare a yeast extract solution. The yeast extract solution was used to test the ratio of free amino acids generated with the enzyme preparation of the invention. For comparison, the same test was conducted by using Protease N "Amano" described above.

Specifically, a given unit quantity of the enzyme preparation of the invention or Protease N "Amano" was added to the extract solution, for reaction at 50° C. for 17 hours and heating at 90° C. for 20 minutes. The resulting enzyme-treated solution was subjected to amino acid analysis to calculate the generation ratio of free amino acids. Herein, the quantity of the enzyme preparation added is expressed on a protease activity basis per 1 g of yeast extract powder.

The results of comparison between the enzyme preparation of the invention and the enzyme preparation Protease N "Amano" are shown in Table 4. As apparently shown in Table 4, the group treated with the enzyme preparation of the invention was at a high generation ratio of free amino acids, had great Umami (deliciousness) without any bitterness and had excellent characteristic properties as yeast extract.

TABLE 4

| Added enzyme activity | Enzyme prep. of the invention | | Protease N "Amano" | |
|---|---|---|---|---|
| | Ratio (%) of free amino acids | Flavor | Ratio (%) of free amino acids | Flavor |
| 100 units | 60% | Umami (delicious) with no bitterness | 20% | Strong bitterness |
| 200 | 68 | Umami (delicious) with no bitterness | 28 | Strong bitterness |
| 300 | 70 | Umami (delicious) with no bitterness | 30 | Strong bitterness |

Industrial Applicability

As described above, the enzyme solution and enzyme preparation of the invention, as obtained by cultivating the *Bacillus subtilis* M2-4 strain, are excellent in heat resistance, the potency of hydrolyzing proteins into low molecules and the potency of hydrolyzing protein hard to be hydrolyzed. Therefore, the enzyme solution and enzyme preparation of the invention can be favorably used for production of amino acid seasoning, bread production, meat tenderization, hydrolysis of soybean protein and the like.

What is claimed is:

1. A method for producing an isolated peptidase solution, comprising cultivating *Bacillus subtilis* M2-4 strain (FERM BP-7155) to produce a culture, wherein said *Bacillus subtilis* M2-4 strain (FERM BP-7155) is isolated from dough of Mantou, and obtaining the peptidase solution from the culture, wherein said peptidase solution is highly heat resistant such that the residual activity thereof after 1-hr heat treatment at 60 to 65° C. at pH 7 is substantially 100%.

2. The method of claim 1, wherein the peptidase solution also has protease and collagenase activity.

3. The method of claim 2, wherein said peptidase solution has aminopeptidase activity.

4. The method of claim 1, wherein said peptidase solution also has protease activity.

5. The method of claim 4, wherein said protease activity is neutral protease activity.

6. The method of claim 4, wherein said protease activity is alkaline protease activity.

7. The method of claim 1, wherein said peptidase solution also has collagenase activity.

* * * * *